United States Patent [19]

Bach, Jr. et al.

[11] Patent Number: 5,105,809

[45] Date of Patent: Apr. 21, 1992

[54] SYSTEM AND METHOD FOR EVALUATING LEAD DEFIBRILLATION REQUIREMENTS OF AN IMPLANTED DEVICE WITHOUT REPEATED FIBRILLATION INDUCTION

[75] Inventors: Stanley M. Bach, Jr., Shoreview; Douglas J. Lang, Arden Hills, both of Minn.; Raymond E. Ideker; J. Marcus Wharton, both of Durham, N.C.

[73] Assignees: Cardiac Pacemakers, Inc., St. Paul, Minn.; Duke University, Durham, N.C.

[21] Appl. No.: 571,234

[22] Filed: Aug. 23, 1990

[51] Int. Cl.⁵ .............................................. A61N 1/39
[52] U.S. Cl. ................................. 128/419 D; 128/697
[58] Field of Search ............................ 128/419 D, 697

[56] References Cited

PUBLICATIONS

Hoffman et al., "Vulnerability to Fibrillation and the Ventricular-Excitability Curve", 88-94, American Journal of Physiology, Oct. 1951, vol. 167.
Han, "Ventricular Vulnerability to Fibrillation", 87-95, In: Dreifus, Lihoff, editors: Cardiac Arrhythmias, NY 1973, Grune & Stratton, Inc.
Wiggers et al., "Ventricular Fibrillation Due to Single, Localized Induction and Condenser Shocks Applied During the Vulnerable Phase of Ventricular Systole", 500-505, American Journal of Physiology, 1940, vol. 128.
Chen et al., "Comparison of the Defibrillation Threshold and the Upper Limit of Ventricular Vulnerability", 1022-1028, Circulation, 1986, vol. 73.

*Primary Examiner*—William E. Kamm
*Assistant Examiner*—Scott M. Getzow
*Attorney, Agent, or Firm*—Fleit, Jacobson, Cohn, Price, Holman & Stern

[57] ABSTRACT

A system for determining the defibrillation threshold energy of a defibrillation lead arrangement by shocking the heart during the T wave of the ECG at decreasing energy levels until the heart is placed in fibrillation. The lowest energy level tested which fails to place the heart in fibrillation correlates to the defibrillation threshold energy of the lead arrangement.

20 Claims, 2 Drawing Sheets

SYSTEM AND METHOD FOR EVALUATING LEAD DEFIBRILLATION REQUIREMENTS OF AN IMPLANTED DEVICE WITHOUT REPEATED FIBRILLATION INDUCTION

BACKGROUND OF THE INVENTION

The present invention relates to a system for determining the effective defibrillation energy discharged in an implantable defibrillation system without repeatedly inducing fibrillation of the patient's heart.

In the field of implantable defibrillation, it is well known that the energy level necessary for effecting defibrillation of a patient's heart varies with internal defibrillation lead configuration and placement, as well as the responsiveness of a particular patient's heart. It is necessary to determine, with the highest degree of accuracy, the minimal energy level necessary to defibrillate a patient's heart.

One known method to determine the defibrillation threshold energy of an implantable system is to induce fibrillation of a patient's heart. Once fibrillation is achieved, the heart is defibrillated through the implanted defibrillation leads. Initially, defibrillation is attempted at a relatively high energy level. If this energy level defibrillates the heart, the heart is placed in fibrillation again, and a defibrillation pulse of a lower energy level is applied to the heart. If this energy level defibrillates the heart, the process is repeated with lower defibrillation pulse energy levels until the heart is not defibrillated. Fibrillation-defibrillation episodes are often repeated at the lowest initially successful energy to obtain an estimate of that energy's probability for success, since an actual threshold does not exist. Finally, the defibrillation energy level for the permanently implanted device initially is set above that energy level which reliably defibrillated the heart, depending upon the decision of the physician.

A disadvantage of the above-described method is the need to repeatedly induce fibrillation of the heart, and to repeatedly defibrillate the heart to determine system thresholds.

SUMMARY OF THE INVENTION

It is a primary object of the present invention to overcome the above-stated problems by determining the minimal defibrillation energy needed by an implanted system without repeatedly inducing fibrillation of a patient's heart.

It is an additional object of this invention to determine the minimal defibrillation energy by shocking the heart during the vulnerable period indicated by signals representative of the electrical activity of the heart.

The present invention relates to a system and method for determining the minimal defibrillation energy required to defibrillate a patient's heart with an implanted system by sensing the cardiac depolarization (QRS complex) of a heart not in arrhythmia, and delivering a shock to the heart after a predetermined period of time at the occurrence of the vulnerable period. Specifically, the shock is delivered to the heart during the T wave, known as the vulnerable period, with different shock strengths. Alternatively, the heart may be paced so that detection of the QRS complex is not made to determine the occurrence of the vulnerable period. Rather, because the heart is paced, precise prediction of the occurrence of the vulnerable period is made by controlling the pacing.

While shocks with sufficient strength will induce ventricular fibrillation, as the strength is increased into an upper range, a shock level or strength will be reached which no longer produces ventricular fibrillation. The lowest strength in this upper range which fails to fibrillate the heart correlates with the strength needed to defibrillate the heart. As such, repeated fibrillation of the heart is avoided by this method.

The above and other objects and advantages will become more readily apparent when reference is made to the following description, taken in conjunction with the accompanying drawings.

DETAILED DESCRIPTION OF THE DRAWINGS

Figure 1:
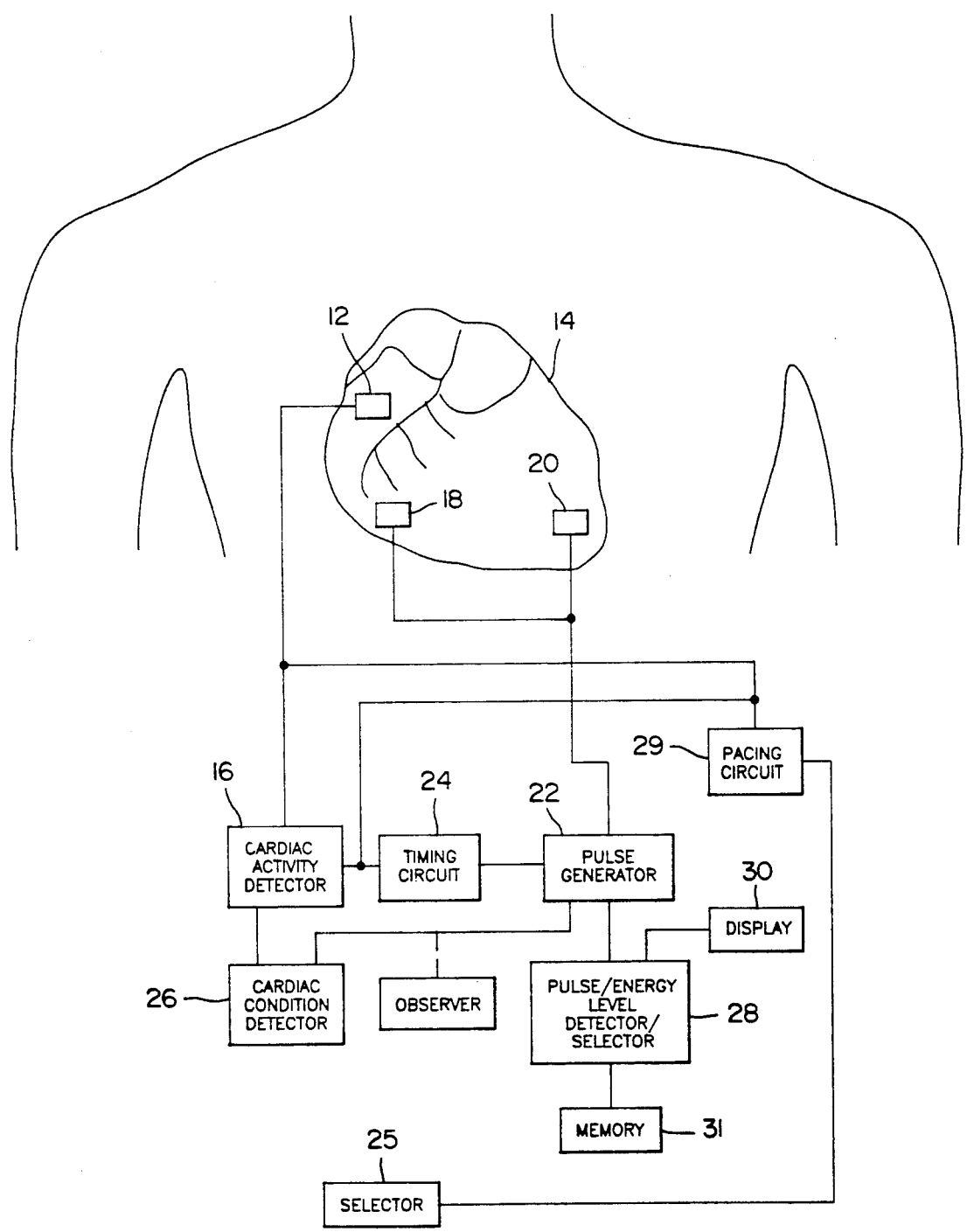
FIG. 1 is a schematic block diagram illustrating the system for determining the threshold defibrillation energy of a particular patient with a particular implanted defibrillation device, in accordance with the present invention.

Referring first to FIG. 1, the defibrillation threshold determination system is generally shown at 10. The system 10 includes a sensing electrode 12 implanted on or about the heart 14 of a patient and connected to cardiac activity detector 16. The term "on or about the heart" is meant to include subcutaneously or externally on the chest of a patient. The position of the sensing electrode 12 is not critical so long as an accurate indication of the electrical activity of the heart can be obtained. As one example, the sensing electrode may be a pacing/sensing tip electrode.

The cardiac activity detector 16 may be, for example, an ECG detector, which includes an amplifier for amplifying the level of the signal sensed at electrode 12. The purpose of the cardiac activity detector is to determine the occurrence of the vulnerable period of the electrical activity of the heart. Two additional defibrillation electrodes 18 and 20 are provided and implanted on or about the heart, and connected to a pulse generator 22. The pulse generator 22 is connected to the cardiac activity detector 16 by a timing circuit 24.

A cardiac condition detector 26 is provided and connected to the cardiac activity detector 16 for monitoring the functional condition of the heart. A pulse/energy level detector 28 is provided and connected to pulse generator 22 for selecting the level of energy of the shock delivered to the heart. The value of the pulse/energy level detector 28 can be visually monitored on the display unit 30 and stored in the memory 31, both of which are connected to the detector 28. The function of the cardiac condition detector 26 to detect fibrillation can also be accomplished by an observer, as shown in the figure.

Often, a patient's heart must be paced during the procedure according to the present invention because, for example, the heart cannot properly function alone. To accommodate such a patient, the present invention employs a pacer circuit 29. The pacing circuit 29 is connected to the timing circuit 24 and to the electrode 12 which serves as a pacing/sensing electrode. In addition, a selector 25 is provided to enable the pacing circuit 29 to be active at the discretion of the user. In this arrangement, the occurrence of the vulnerable period is determined directly from the pacing circuit 29 through the timing circuit 24 without use of the cardiac activity detector 16.

The system 10 operates as follows. For a heart not in arrhythmia, the electrical activity of the heart 14 is sensed by the detector 16 via the electrode 12. The detector 16 senses cardiac depolarization, or the QRS complex which triggers the timing circuit 24. The timing circuit 24, upon being triggered by the detector 16 and after a predetermined time delay, triggers the pulse generator 22 to deliver a shock to the heart 14 between the electrodes 18 and 20. The time delay of the timing circuit 24 corresponds to the time delay between the occurrence of the QRS complex and the vulnerable period corresponding to the T wave.

Alternatively, for a heart requiring pacing, the pacing circuit 29 paces the heart via electrode 12 and the timing circuit 24 is triggered by the pacing circuit 29 to control the shock delivered to the heart by the pulse generator 22.

Figure 2:
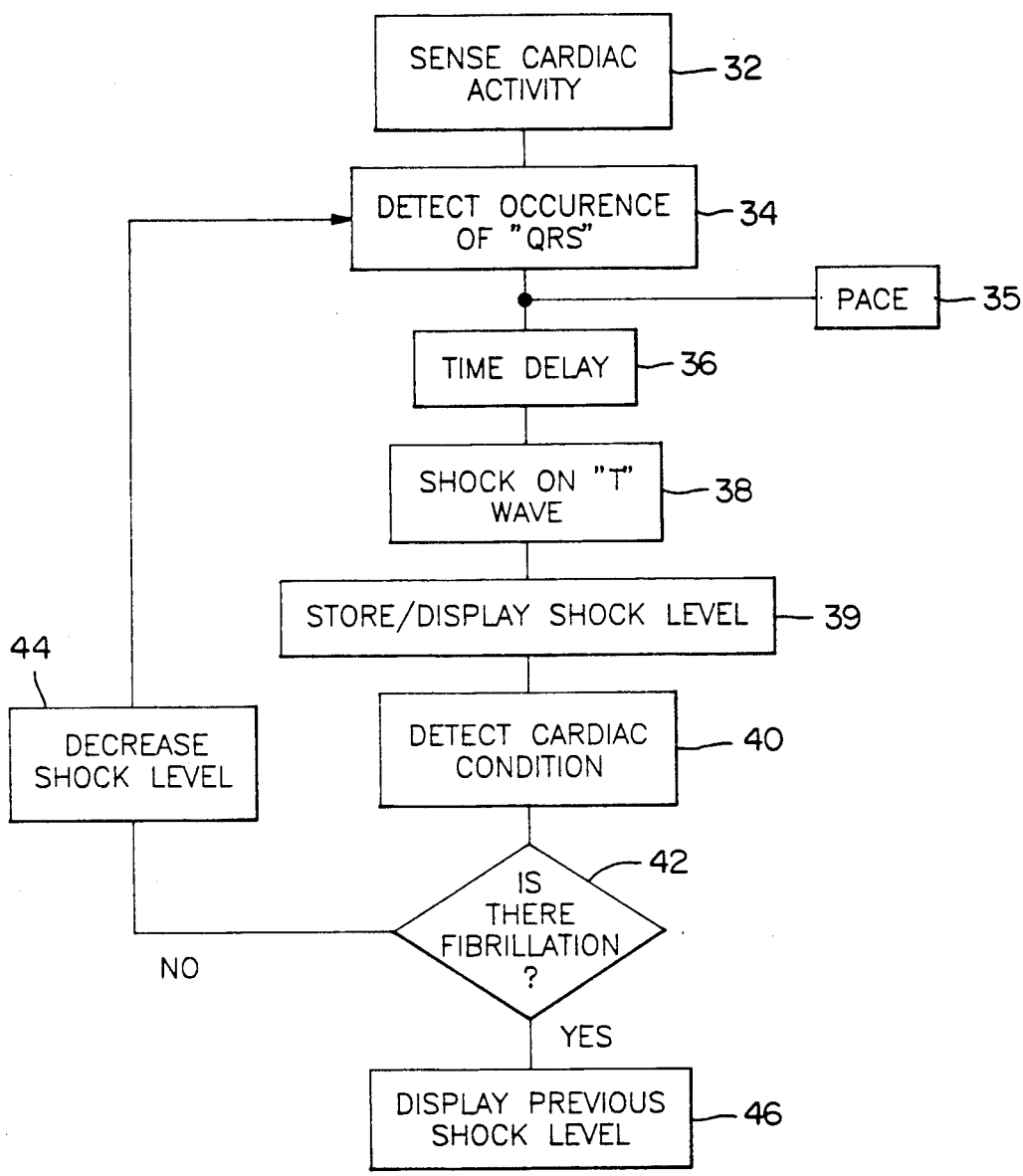
FIG. 2 is a block diagram illustrating the steps for determining the required defibrillation energy for a particular patient in accordance with the present invention.
Figure 3:
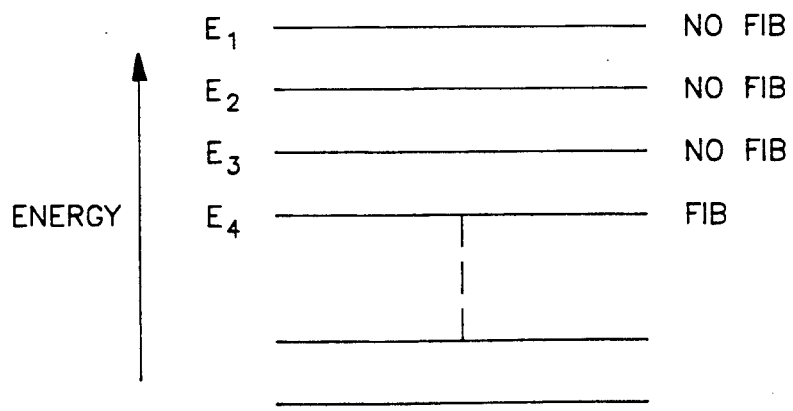
FIG. 3 is a diagram illustrating the relationship between the applied energy levels and the threshold defibrillation energy.

Referring now to FIGS. 1, 2, and 3, the operation of the system 10 will be described in more detail. For a heart not in arrhythmia, in step 32, the cardiac activity detector 16 senses the electrical activity of the heart 14. Once the occurrence of the QRS complex is detected by the detector 16 in step 34, the timing circuit 24 is activated to et a predetermined time delay prior to shocking the heart, in step 36. As shown, step 35 replaces steps 32 and 34 for a heart requiring pacing. At the end of the time delay, the pulse generator 22 is triggered by the timing circuit 24 to apply a shock to the heart via electrodes 18 and 20 at the occurrence of the T wave, in step 38.

Initially, as shown in FIG. 3, the energy level $E_1$ of the shock applied to the heart is relatively high at which fibrillation will likely not be induced. The energy level is stored in memory 31 and/or displayed on display 30 at step 39 and the cardiac condition detector 26 examines the signal from the detector 16 to determine whether the heart is placed into fibrillation by the shock from the pulse generator 22, in steps 40 and 42. If the heart is not placed in fibrillation, the next shock applied by the pulse generator 22 is decreased to a lower energy level, such as $E_2$, by the pulse/energy level detector/selector 28, in step 44. Thereafter, steps 34-42 are repeated until the heart is placed in fibrillation. Typically, the increments of shock energy levels are on the order of 5 Joules, and the shocks are electrical pulses of the truncated exponential, mono, or biphasic type of waveforms.

Once the heart is placed in fibrillation, as shown by $E_4$, the previous energy level $E_3$ stored in the memory 31 is displayed on the display unit 30 in step 46. Energy level $E_3$ corresponds to the threshold defibrillation level for the particular lead configuration. Then, the heart is defibrillated by applying a defibrillation pulse of sufficient energy level through electrodes 18 and 20.

By the above-described system, the number of times a patient is placed in fibrillation when implanting a new defibrillation system is reduced. Thus, unnecessary risk and trauma to the patient is avoided.

Modifications such as, for example, combining the functions of the cardiac activity detector 16 and the cardiac condition detector 26 into a single unit are considered within the scope and spirit of the present invention. In addition, the system according to the present invention can be used to determine the threshold defibrillation energy of a lead arrangement having more than two defibrillation electrodes of any type, such as patch, cup, and catheter electrodes.

The above description is intended by way of example only and is not intended to limit the present invention in any way except as set forth in the following claims.

We claim:

1. A system for determining the defibrillation threshold energy of a defibrillation lead arrangement implanted in a patient and including at least two defibrillation electrodes implanted on or about the heart, said system comprising:

sensing means for sensing the electrical activity of the heart;

detector means connected to said sensing means for detecting electrical events of the heart on the basis of said sensed electrical activity of the heart and determining the vulnerable period of said electrical activity;

pulse generator means connected to said detector means and for generating and delivering an electrical pulse to the heart via said defibrillation electrodes during the vulnerable period of the electrical activity of the heart;

pulse energy level detector/selector means connected to said pulse generator means for controlling the energy level of the electrical pulse generated and delivered by said pulse generator means;

memory means for storing the energy level of the electrical pulse delivered by the pulse generator means; and wherein said pulse generator means delivers an initial electrical pulse to the heart at a predetermined initial energy and continues to deliver subsequent electrical pulses to the heart with decreasing energies under control of said pulse energy level detector/selector means until the heart is induced to fibrillate as determined by said detector means, and upon which the energy level of the electrical pulse immediately prior to the electrical pulse which induced the heart to fibrillate, correlates to the defibrillation threshold energy of said defibrillation lead arrangement.

2. The system of claim 1, and further comprising timing means connected to said detector means and said pulse generator means for determining the occurrence of said vulnerable period by a predetermined time delay subsequent to a predetermined electrical event of the heart.

3. The system of claim 2, wherein said detector means detects the ECG of the heart and said predetermined electrical event is the QRS complex and said vulnerable period is the T-wave of the ECG of the heart.

4. The system of claim 1, and further comprising display means for displaying the energy level of the electrical pulse generated and delivered by said pulse generator.

5. The system of claim 1, and further comprising pacing means and a pacing electrode implanted on or about the heart.

6. A method for determining the defibrillation threshold energy of a defibrillation lead arrangement implanted in a patient and including at least two defibrillation electrodes implanted on or about the heart, said method comprising the steps of:

determining the occurrence of the vulnerable period of the electrical activity of the heart;

delivering an electrical pulse to the heart via said 2 defibrillation electrodes at decreasing energy levels starting with an initial energy level until the heart is induced to fibrillate;

storing the energy level immediately greater than the energy level of the electrical pulse which induced the heart to fibrillate.

7. A method for determining the defibrillation threshold energy of a defibrillation lead arrangement implanted in a patient and including at least two defibrillation electrodes implanted on or about the heart, said method comprising the steps of:

pacing the heart;

determining the occurrence of the vulnerable period of the electrical activity of the heart;

delivering an electrical pulse to the heart via said defibrillation electrodes at decreasing energy levels starting with an initial energy level until the heart is induced to fibrillate;

storing the energy level immediately greater than the energy level of the electrical pulse which induced the heart to fibrillate.

8. A method for determining the defibrillation threshold energy of a defibrillation lead arrangement implanted in a patient and including at least two defibrillation electrodes implanted on or about the heart, said method comprising the steps of:

(a) determining the occurrence of the vulnerable period of electrical activity of the heart;

(b) delivering an electrical pulse to the heart via said defibrillation electrodes at a predetermined energy level during said vulnerable period;

(c) storing said predetermined energy level;

(d) determining whether the heart is placed in fibrillation by said electrical pulse;

(e) decreasing said predetermined energy level by a predetermined amount if fibrillation is not effected and repeating steps (a)-(d) until the heart is placed in fibrillation; and (f) recalling the lowest predetermined energy level which failed to place the heart in fibrillation immediately above the predetermined energy level which induced fibrillation.

9. The method of claim 8, wherein said step of determining comprises sensing the ECG of the heart and the QRS complex of the ECG to determine the occurrence of the T-wave which corresponds to the vulnerable period.

10. The method of claim 8, and further comprising the step of pacing the heart.

11. The method of claim 8, and further comprising the step of displaying each predetermined energy level.

12. A method for determining the defibrillation threshold energy of a defibrillation lead arrangement including at least two defibrillation electrodes implanted on or about the heart, said method comprising the steps of:

(a) sensing the electrical activity of the heart;

(b) determining the occurrence of the vulnerable period of the electrical activity;

(c) delivering an electrical pulse to the heart via said electrodes at a predetermined energy level during the vulnerable period;

(d) determining whether the heart is placed in fibrillation by said electrical pulse;

(e) decreasing said predetermined energy level by a predetermined amount and repeating steps (a)-(d) until the heart is placed in fibrillation; and (f) storing the lowest predetermined energy level which failed to place the heart in fibrillation immediately above the predetermined energy level which induced fibrillation.

13. The method of claim 12, and further comprising the steps of storing and displaying each predetermined energy level.

14. A system for determining the defibrillation threshold energy of a defibrillation lead arrangement, said system comprising:

defibrillation electrodes mounted on or about the heart;

sensing electrode means mounted on or about the heart to sense the electrical activity of the heart of a patient to determine the ECG of the patient;

means for determining the vulnerable period from the said ECG;

means for delivering shocks of decreasing energy levels via said defibrillation electrodes to the heart during said vulnerable period;

means for sensing and determining whether said shocks delivered by said means for delivering induces ventricular fibrillation in the patient's heart;

means for storing the lowest energy level of the shock failing to induce ventricular fibrillation immediately above the shock which induces ventricular fibrillation.

15. The system of claim 14, wherein said means for determining the patient's vulnerable period determines the occurrence of the T wave of said ECG as said vulnerable period.

16. A method for determining the defibrillation threshold energy of a defibrillation lead arrangement, said method comprising the steps of:

implanting defibrillation electrodes on or about the heart of a patient;

sensing the electrical activity of the heart and determining the vulnerable period of the electrical activity;

shocking the heart at the vulnerable period with shocks decreasing in energy levels;

determining the lowest energy level of the shock which failed to induce ventricular fibrillation immediately above the energy level of the shock which induces fibrillation;

using said lowest energy level as an indicator of the defibrillation threshold energy of said implanted defibrillation electrodes in that particular patient.

17. The method of claim 16, wherein said step of sensing the electrical activity of the heart determines ECG of the heart and the T wave of the ECG as the vulnerable period.

18. A system for determining the defibrillation threshold energy of a defibrillation lead arrangement implanted in a patient and including at least two defibrillation electrodes implanted on or about the heart, said system comprising:

sensing means for sensing the electrical activity of the heart;

pacing means and pacing electrode means connected to said pacing means for delivering electrical pacing signals to the heart;

detector means connected to said sensing means for detecting electrical events of the heart on the basis of said sensed electrical activity of the heart;

pulse generator means connected to said detector means and for generating and delivering an electrical pulse to the heart via said defibrillations electrodes during the vulnerable period of the electrical activity of the heart;

pulse energy level detector/selector means connected to said pulse generator means for controlling the energy level of the electrical pulse generated and delivered by said pulse generator means;

memory means for storing the energy level of the electrical pulse delivered by the pulse generator means; and wherein said pulse generator means delivers an initial electrical pulse to the heart at a predetermined initial energy and continues to deliver subsequent electrical pulses to the heart with decreasing energies under control of said pulse energy level detector/selector means until the heart is induced to fibrillate as determined by said detector means, and upon which the energy level of the electrical pulse immediately prior to and above that which induced the heart to fibrillate correlates with the defibrillation threshold energy of said defibrillation lead arrangement.

19. The system of claim 18, and further comprising timing means connected to said pacing means and said pulse generator means for determining the occurrence of said vulnerable period by a predetermined time delay subsequent to a predetermined electrical event provided by said pacing means.

20. The system of claim 18, and further comprising display means for displaying the energy level of the electrical pulse generated and delivered by said pulse generator.

* * * * *